United States Patent
Hermelin et al.

(10) Patent No.: US 6,576,666 B2
(45) Date of Patent: Jun. 10, 2003

(54) NUTRITIONAL SUPPLEMENTS

(75) Inventors: Marc S. Hermelin, Glendale, MO (US); R. Saul Levinson, Chasterfield, MO (US); George Paradissis, St. Louis, MO (US)

(73) Assignee: Drugtech Corporation, Wilmington, DE (US)

(*) Notice: Subject to any disclaimer, the term of this patent is extended or adjusted under 35 U.S.C. 154(b) by 0 days.

(21) Appl. No.: 09/885,158

(22) Filed: Jun. 21, 2001

(65) Prior Publication Data

US 2002/0032234 A1 Mar. 14, 2002

Related U.S. Application Data

(63) Continuation of application No. 09/323,159, filed on Jun. 1, 1999, now Pat. No. 6,258,846.

(51) Int. Cl.$^7$ .................. A61K 31/20; A61K 31/44; A61K 31/495; A61K 31/50; A61K 31/34
(52) U.S. Cl. .................. 514/560; 514/345; 514/249; 514/474; 514/458
(58) Field of Search .................. 514/560, 345, 514/249, 474, 458

(56) References Cited

U.S. PATENT DOCUMENTS

| | | | |
|---|---|---|---|
| 3,925,560 A | 12/1975 | Scott et al. | 426/2 |
| 4,642,317 A | 2/1987 | Palmquist et al. | 514/588 |
| 4,753,926 A | * 6/1988 | Lucas et al. | 514/2 |
| 5,004,728 A | 4/1991 | Chalupa et al. | 514/12 |
| 5,143,737 A | 9/1992 | Richardson | 426/2 |
| 5,264,217 A | 11/1993 | Horrobin | 424/439 |
| 5,562,913 A | 10/1996 | Horrobin | 424/401 |
| 5,635,198 A | 6/1997 | Nishimura et al. | 424/438 |
| 5,744,161 A | 4/1998 | Majeed et al. | 424/464 |
| 5,776,504 A | 7/1998 | McCarty | 424/682 |

OTHER PUBLICATIONS

Clark et al, 117CA:25288, 1992.*
FDA (United States Food and Drug Administration), 104CA:4736, 1985.*
Alvarez et al. 107CA:22135, 1986.*
The Merck Manual 185: 968 (16$^{th}$ Ed. 1992).
The Merck Manual 185: 1929–1931 (16$^{th}$ Ed. 1992).
Physician Desk Reference (PDR), 53$^{rd}$ Ed., 1011, 1999.
Physician Desk Reference (PDR), 53$^{rd}$ Ed., 1522–3, 1999.
Physician Desk Reference (PDR), 53$^{rd}$ Ed., 1692, 1999.
Physician Desk Reference (PDR), 53$^{rd}$ Ed., 2802, 1999.
Physician Desk Reference (PDR), 53$^{rd}$ Ed., 2916–17, 1999.
Physician Desk Reference (PDR), 53$^{rd}$ Ed., 2917–18, 1999.
Physician Desk Reference (PDR), 53$^{rd}$ Ed., 3128, 1999.
Physician Desk Reference (PDR), 53$^{rd}$ Ed., 3163, 1999.
Physician Desk Reference (PDR), 53$^{rd}$ Ed., 3212, 1999.
Whitney, E. and Rolfes, S., *Understanding Nutrition*, 6$^{th}$ Ed., 136–40, 1993.
Whitney, E. and Rolfes, S., *Understanding Nutrition*, 6$^{th}$ Ed., 493–504, 1993.

* cited by examiner

Primary Examiner—Russell Travers
(74) Attorney, Agent, or Firm—Nath & Associates PLLC; Gary M. Nath

(57) ABSTRACT

The present disclosure relates to novel nutritional compositions containing linoleic acid and/or linolenic acid which optimize child neurological development and provide improved nutritional support for women prior to and during lactation. The nutritional compositions are intended for use by women to optimize infant neurological development and provide improved nutritional support for women prior to, during and after lactation.

23 Claims, No Drawings

NUTRITIONAL SUPPLEMENTS

This application is a continuation application of U.S. patent application Ser. No. 09/323,159, filed Jun. 1, 1999 now U.S. Pat. No. 6,258,846, the entire contents of which are hereby incorporated by reference in their entirety.

BACKGROUND OF THE INVENTION

1. Field of the Invention

The present invention is directed to novel compositions containing fatty acids, in particular, linoleic acid and linolenic acid, for use by pregnant and/or lactating women to optimize infant neurological development and provide improved nutritional support for women prior to, during and after lactation.

2. Description of the Related Art

At some time prior to the end of pregnancy, pregnant women face the decision of whether or not to breast-feed their infants. It is estimated that over 50% of all mothers choose to breast-feed their infants. See *The Merck Manual,* 185:1929–1931 ($16^{th}$ ed. 1992). Furthermore, the number of women deciding to breast-feed appears to be on the increase, particularly in higher socioeconomic groups. Id. Most experts would agree that this increase is very desirable in view of the numerous recognized nutritional benefits for developing infants which accompany their consumption of human milk. Because of the nutritional benefits for infants, many health care providers and dietitians believe breast-feeding is sufficiently important to warrant that every effort be made to breast-feed, even if only for a short time. See Whitney et al., *Understanding Nutrition,* 493–504 ($6^{th}$ ed. 1993).

Moreover, in addition to the nutritional benefits of breast-feeding, many women simply want to breast-feed their infants for emotional or psychological reasons. However, regardless of a women's underlying reasons for breast-feeding, her nutritional status is implicated in the decision of whether to breast-feed her child. For example, a nutritional deficiency in a woman may severely limit the quantity of breast milk which is produced or, in some cases, entirely prevent lactation from occurring.

Generally speaking, the nutritional benefits of breast-feeding stem from the unique nutrient composition and protective factors present in breast milk which promote infant health and development. Id. at 494. For example, breast milk generally contains all of the vitamins required for infant development, with the possible exception of vitamin D. Id. at 500. Further, breast milk is an abundant source of minerals and, more importantly, some minerals are present in breast milk in highly desirable ratios (e.g., the 2-to-1 ratio of calcium to phosphorus in breast milk is ideal for the absorption of calcium). Id. Breast milk also contains invaluable immunological agents, including antiviral agents such as immunoglobulins, and antibacterial agents such as lactoferrin.

In addition to the above discussed vitamins, minerals and immunological agents, breast milk also contains various "energy nutrients". For example, breast milk contains lactose which is the carbohydrate present in breast milk and which facilitates calcium absorption. Id. A relatively small amount of protein, primarily in the form of alpha-lactalbumin, is also present in breast milk, thus placing less stress on the infant's immature kidneys. Id. Breast milk additionally contains fat along with fat-digesting enzymes. Id. Linoleic acid, a fatty acid, is found in large quantities in breast milk. Id.

The presence of fatty acids in breast milk is significant for various reasons, as described below. First, the body derives most of its energy from triglycerides, a molecule of glycerol with three fatty acids attached. The stored fatty acids support most of life's activities when individual's are between meals or must go without food. While the body can make many fatty acids, it cannot make linoleic acid or linolenic acid. These two fatty acids are indispensable to body functions and therefore must be supplied through food.

Secondly, essential fatty acids are important for the developing brain, immunological system and cardiovascular system, and have some role to play in every organ of the body. Linoleic acid is the most important member of the omega-6 family of fatty acids. The body uses linoleic acid to synthesize an important 20-carbon fatty acid, arachidonic acid, which helps maintain the structural integrity of cell membranes.

Linolenic acid is the most important member of the omega-3 family of fatty acids. The body requires this fatty acid to make eicosapentaenoic acid (EPA) and docosahexaenoic acid (DHA). Many body tissues require EPA and DHA. DHA is especially important in the retina and in the cerebral cortex of the brain. Half of the DHA in a fetus's body accumulates in the brain before birth, and half after birth, an indication of the importance of fatty acids to the fetus during pregnancy and then to the young infant during lactation.

Successful breast-feeding requires that the mother maintain good nutrition and adequate rest. A good, nutritional diet is needed to support the stamina that nursing an infant requires. Beyond this, however, a woman must consume a nutrient-rich diet to produce nutrient-rich milk.

A healthy nursing mother generally makes about 25 ounces of milk each day. To produce this milk, the mother needs to consume 650 kcalories above what she would normally require for herself. Woman are advised to eat about 500 kcalories worth of extra food and let the extra fat left over from pregnancy provide the rest. Woman may not consume enough food for many reasons, including the desire to lose all of the weight gained during pregnancy. But restricting food and energy in this fashion will result in breast milk which is lacking in nutrients, low quantities of breast milk or, in the worse case scenario, no breast milk at all.

According to the medical literature, a nursing mother should eat foods high in nutrients and drink plenty of fluid. Nutritional deprivation in the mother generally reduces the quantity, more so than the quality, of the milk. So while woman can produce milk with sufficient protein, carbohydrate, fat and minerals even if their own intake is insufficient, the quality of the breast milk is maintained at the expense of the mother's own nutrient repositories. Moreover, quantities of particular vitamins, such as B6, B12, A and D, in breast milk will actually decline in response to a inadequate intakes by the mother.

Infants have different nutritional needs than those of children and adults. They require more fat and less protein than adults. Breast milk contains high concentrations of fat-digesting enzymes that allow for highly efficient fat absorption. Breast milk, as well as colostrum, contain the essential fatty acid linoleic acid. *Understanding Nutrition,* Whitney and Rolfe, $6^{th}$ Ed., 136–40 (1993).

Full term babies who are not fed enough linoleic acid suffer from dermatosis and growth failure. These conditions are easily reversed when linoleic acid is added to the infant's diet. Fatty acid deficiency in a breast-feeding infant is a hazzard of long term low fat parental dieting. *The Merck Manual*, 16$^{th}$ Ed., 968 (1992).

Methods of administering linolenic acid to lactating females have been previously described. Specifically, Horrobin, U.S. Pat. No. 5,264,217, discloses methods for increasing the total fat content of milk, the essential fatty acid content of milk and the flow of milk during lactation, or for preventing or reducing the normal decrease in milk fat content that occurs during prolonged lactation, by administering gamma linolenic acid, dihomo-gamma-linolenic acid or their mixture to a lactating female.

Other references disclose compositions and methods that have been developed for achieving fat enrichment of ruminant milk for consumption by humans. In general, animal feed is supplemented with fatty acids. In turn, the milk produced by the ruminants is itself rich in fatty acids.

Chalupa et al., U.S. Pat. No. 5,004,728, describe a method for increasing milk yields in lactating ruminants. The ruminants are fed somatotropin and salts of long chain fatty acids. The fatty acids in the feed increases the level of long chain fatty acids in the milk produced by the ruminant. One long chain fatty acid suitable for this inventive subject matter is linoleic acid.

Nishimura et al., U.S. Pat. No. 5,635,198, describe a granular agent comprised by an active core coated by certain fatty acids and oils to be administered to ruminants. This granular agent has a superior absorption rate and results in, among other benefits, efficient lactation in the ruminant.

Scott et al., U.S. Pat. No. 3,925,560, describe a feed supplement for ruminants comprising fatty acids encapsulated with a protein-aldehyde reaction product. These fatty acid supplements, including linoleic acid, provide high energy feed supplements for ruminants. These supplements will result in the ruminate producing a milk very high in unsaturated fats.

Palmquist et al., U.S. Pat. No. 4,642,317, describe a process for feeding ruminants fatty acids in the form of their calcium salts, which are added to feed. This process would allow dairy cows to make milk high in fats, without depleting their own fatty acid stores.

Richardson, U.S. Pat. No. 5,143,737, describes a method for the modification of ruminant food so that the ruminant will produce a milk with modified fat. This method comprises a non-toxic food to be surrounded by an acid-sensitive nontoxic crosslinking material. Animals eating this composition will make milk with a higher level of unsaturated fats.

Furthermore, several prenatal supplements are available which provide pregnant women with varying amounts of vitamins and minerals. The *Physicians' Desk Reference* describes various vitamin and mineral supplements for use by pregnant women. For example, Nestabs® CBF, prenatal formula, available from The Fielding Company, Maryland Heights, Mo., contains 4,000 I.U. of vitamin A, 400 I.U. of vitamin D, 30 I.U. of vitamin E, 120 mg of vitamin C, 1 mg of folic acid, 3 mg of thiamine, 3 mg of riboflavin, 20 mg of niacinamide, 3 mg of pyridoxine, 8 mcg of vitamin $B_{12}$, 20 mg of calcium, 100 mcg of iodine, 15 mg of zinc, and 50 mg of iron per dose. NESTABS® CBF are "expressly formulated for use during pregnancy and lactation" and are available only in tablet form. See *Physicians' Desk Reference*, (53d Ed., 1999) 1011.

Materna® prenatal vitamin and mineral formula, available from Lederle Laboratories, Pearl River, N.Y., contains 5,000 I.U. of vitamin A, 400 I.U. of vitamin D, 30 I.U. of vitamin E, 120 mg of vitamin C, 1 mg of folic acid, 3 mg of vitamin $B_1$, 3.4 mg of vitamin $B_2$, 10 mg of vitamin $B_6$, 20 mg of niacinamide, 12 mcg of vitamin $B_{12}$, 30 mcg of biotin, 10 mg of pantothenic acid, 200 mg of calcium, 150 mcg of iodine, 27 mg of iron, 25 mg of magnesium, 2 mg of copper, 25 mg of zinc, 25 mg of chromium, 25 mg of molybdenum, 5 mg of manganese, and 20 mcg of selenium per dose. Materna® is designed "provide vitamin and minerals supplementation prior to conception, throughout pregnancy and during the postnatal period for both lactating and nonlactating mothers" and is available in tablet form only. See Id. at 1522–3.

Enfamil® Natalins® RX multivitamin and multimineral supplements, available from Mead Johnson Nutritionals, Evansville, Ind., provide 4000 I.U. of vitamin A, 80 mg of vitamin C, 400 I.U. of vitamin D, 15 I.U. of vitamin E, 1.5 mg of thiamin, 1.6 mg of riboflavin, 17 mg niacin, 4 mg of vitamin $B_6$, 1 mg of folic acid, 2.5 mcg of vitamin $B_{12}$, 30 mcg of biotin, 7 mg of pantothentic acid, 200 mg of calcium, 54 mg of iron, 25 mg of zinc, and 3 mg of copper per dose. Enfamil® Natalins® RX are "to supplement the diet during pregnancy of lactation" and are available only in tablet form. See Id. at 1692.

Prenate® Ultra™ prenatal vitamins, available from Sanofi Pharmaceuticals, New York, N.Y., contain 90 mg of elemental iron, 150 mcg of iodine, 200 mg of calcium, 2 mg of copper, 25 mg of zinc, 1 mg of folic acid, 2700 I.U. of vitamin A, 400 I.U. of vitamin $D_3$, 30 I.U. of vitamin E, 120 mg of vitamin C, 3 mg of vitamin $B_1$, 304 mg of vitamin $B_2$, 20 mg of vitamin $B_6$, 12 mcg of vitamin $B_{12}$, 20 mg of niacinamide, and 50 mg of docusate sodium per dose. Prenate® Ultra™ is "indicated for use in improving the nutritional status of women throughout pregnancy and in the postnatal period for both lactating and nonlactating mothers and is only available in tablet form. See Id. at 2802.

Niferex®-PN formula, available from Schwarz Pharma, Inc., Milwaukee, Wis., contains 60 mg of iron, 1 mg of folic acid, 50 mg of vitamin C, 3 mcg of vitamin $B_{12}$, 4,000 I.U. of vitamin A, 400 I.U. of vitamin D, 2.43 mg of vitamin $B_1$, 3 mg of vitamin $B_2$, 1.64 mg of vitamin $B_6$, 10 mg of niacinamide, 125 mg of calcium, and 18 mg of zinc per dose. Niferex®-PN is "indicated for prevention and/or treatment of dietary vitamin and mineral deficiencies associated with pregnancy and lactation" and is only available in tablet form. See *Physicians' Desk Reference*, (53d Ed., 1999) 2916–7.

Niferex®-PN Forte formula, available from Schwarz Pharma, Inc., Milwaukee, Wis., contains 60 mg of iron, 1 mg of folic acid, 50 mg of vitamin C, 3 mcg of vitamin $B_{12}$, 5,000 I.U. of vitamin A, 400 I.U. of vitamin D, 30 I.U. of vitamin E, 80 mg of vitamin C, 1 mg of folic acid, 3 mg of vitamin $B_1$, 3.4 mg of vitamin $B_2$, 4 mg of vitamin $B_6$, 20 mg of niacinamide, 12 mcg of vitamin $B_{12}$, 250 mg of calcium, 200 mcg of iodine, 10 mg of magnesium, 2 mg of copper, and 25 mg of zinc per dose. Niferex®-PN is "indicated for prevention and/or treatment of dietary vitamin and mineral deficiencies associated with pregnancy and lactation" and is only available in tablet form. See Id. at 2917–8.

Advanced Formula Zenate® prenatal multivitamin/mineral supplement, available from Solvay Pharmaceuticals, Marietta, Ga., contains 3,000 I.U. of vitamin A, 400 I.U. of vitamin D, 10 I.U. of vitamin E, 70 mg of vitamin C, 1 mg of folic acid, 1.5 mg of vitamin $B_1$, 1.6 mg of vitamin $B_2$, 17 mg of niacin, 2.2 mg of vitamin $B_6$, 2.2 of vitamin $B_{12}$, 200 mg of calcium, 175 mcg of iodine, 65 mg of iron, 100 mg of magnesium, and 15 mg of zinc per dose. Advanced Formula Zenate® is "a dietary adjunct in nutritional stress associated with periconception, pregnancy and lactation" and is only available in tablet form. See Id. at 3128.

Precare® prenatal multi-vitamin/mineral formula, available from UCB Pharma, Inc., Smyrna, Ga., contains 50 mg of vitamin C, 250 mg of calcium, 40 mg of iron, 6 mcg of vitamin D, 3.5 mg of vitamin E, 2 mg of vitamin $B_6$, 1 mg of folic acid, 50 mg of magnesium, 15 mg of zinc and 2 mg of copper per dose. Precare® "is indicated to provide vitamin and mineral supplementation throughout pregnancy and during the postnatel period—for both lactating and nonlactating mothers and is available only in caplet form. See Id. at 3163.

Natafort® prenatal multivitamin, available from Warner Chilcott, Rockaway, N.J., contains 1,000 I.U. pf vitamin A, 400 I.U. of vitamin $D_3$, 11 I.U. of vitamin E, 120 mg of vitamin C, 1 mg of folic acid, 2 mg of thiamine mononitrate, 3 mg of riboflavin, 20 mg of niacinamide, 10 mg of vitamin $B_6$, 12 mcg of vitamin $B_{12}$, and 60 mg of iron per dose. Natafort® is designed "to provide vitamin and mineral supplementation throughout pregnancy and during the postnatal period, for both the lactating and non-lactating mother" and is only available in tablet form. See Id. at 3212.

However, none of the above formulations provide women with essential fatty acids in amounts and proportions necessary to optimize infant neurological development. Further, the prenatal nutritional supplements containing vitamins and minerals are entirely lacking in essential fatty acids. In the case of the enriched ruminant milk, while this milk may be a good source of fatty acids for adults, ruminant milk is not recommended for infants because even supplemented formula cannot match the immunological benefits of breast milk.

Therefore, there remains a need for a nutritional formulation which optimizes infant neurological development. It is also desirable to have nutritional formulations which prevent a woman's stores of fatty acids from becoming depleted during lactation. There is also a particular need for nutritional formulations which provide essential fatty acids in optimal ratios and amounts, along with required vitamins and minerals. Moreover, it is desirable to have formulations and methods which prepare a woman's body for the stresses imposed by lactation.

SUMMARY OF THE INVENTION

The compositions of the present inventive subject matter overcome the deficiencies of currently-available nutritional supplements by providing formulations which are specifically tailored for women during the period prior to and during lactation and which optimize infant neurological development while inhibiting depletion of a nursing mother's nutritional stores. The present compositions contain a novel combination of fatty acids in critical ratios and amounts, optionally in combination with various vitamins and minerals.

In one embodiment of the inventive subject matter, a composition comprises a first fatty acid compound selected from the group consisting of linoleic acid, linolenic acid, a derivative thereof and a combination thereof in an amount ranging from about 10 mg to 100 mg; and a second fatty acid compound selected from the group consisting of a docosahexaenoic acid compound, an omega-3 fatty acid, and omega-2 fatty acid, a derivative thereof and a combination thereof in an amount ranging from about 10 mg to 100 mg; wherein the weight ratio of the first fatty acid compound to the second fatty acid compound is about 1:0.1 to 10.

In another embodiment of the inventive subject matter, a composition comprises a first fatty acid compound selected from the group consisting of linoleic acid, linolenic acid, a derivative thereof and a combination thereof in an amount ranging from 10 mg to 100 mg; a second fatty acid compound selected from the group consisting of a docosahexaenoic acid compound, an omega-3 fatty acid, and omega-2 fatty acid, a derivative thereof and a combination thereof in an amount ranging from about 10 mg to 100 mg; a vitamin B6 compound or derivative thereof in a range of about 20 mg to 125 mg; a folic acid compound or derivative thereof in a range of about 0.1 mg to 3 mg; and a calcium compound or derivative thereof in a range of about 100 mg to 1000 mg. The weight ratio of the first fatty acid compound to the second fatty acid compound is about 1:0.1 to 10.

In a further embodiment of the inventive subject matter, a composition comprises a first fatty acid compound selected from the group consisting of linoleic acid, linolenic acid, a derivative thereof and a combination thereof in an amount ranging from 10 mg to 100 mg; a second fatty acid compound selected from the group consisting of a docosahexaenoic acid compound, an omega-3 fatty acid, and omega-2 fatty acid, a derivative thereof and a combination thereof in an amount ranging from about 10 mg to 100 mg; a vitamin B6 compound or derivative thereof in a range of about 20 mg to 125 mg; a folic acid compound or derivative thereof in a range of about 0.1 mg to 3 mg; a calcium compound or derivative thereof in a range of about 100 mg to 1000 mg; a magnesium compound or derivative thereof in a range of about 25 mg to 400 mg; a vitamin C compound or derivative thereof in a range of 25 mg to 400 mg; and a vitamin E compound or derivative thereof in a range of 10 mg to 400 mg. The weight ratio of the first fatty acid compound in the composition to the second fatty acid compound in the composition is about 1:0.1 to 10.

In a further embodiment of the inventive subject matter, a composition for administration to a female mammal for enriching the milk of said female mammal to optimize neurological development of a neonate being nursed by the female mammal, which comprises about 10 mg to 1000 mg per 55 kg of said mammal's body weight of a first fatty acid compound for each compound selected from the group consisting of a linoleic acid compound, a linolenic acid compound, a derivative thereof and a combination thereof; about 10 mg to 1000 mg of a second fatty acid compound selected from the group consisting of a docosahexaenoic acid compound, an omega-3 fatty acid, an omega-2 fatty acid, a derivative thereof and a combination thereof; and wherein the weight ratio of said first fatty acid compound to said second fatty acid compound is about 1:0.01 to 10.

In yet another embodiment of the inventive subject matter, a composition for administration to a woman for enriching the breast milk of said woman to optimize neurological development of an infant breast-fed by the woman, which comprises about 10 mg to 1000 mg of a first fatty acid compound for each compound selected from the group consisting of a linoleic acid compound, a derivative thereof and a combination thereof; about 10 mg to 1000 mg of a second fatty acid compound selected from the group consisting of a docosahexaenoic acid compound, an omega-3 fatty acid, an omega-2 fatty acid, a derivative thereof and a combination thereof; and wherein the weight ratio of said first fatty acid compound to said second fatty acid compound is about 1:0.01 to 10.

The inventive subject matter also provides a method for enriching the breast milk of a woman to optimize neurological development of her breast-fed infant, which comprises administering a first fatty acid compound to the woman during a period which begins at least at about the tenth week of pregnancy. This first fatty acid compound is selected from the group consisting of a linoleic acid compound, a linolenic acid compound, a derivative thereof and a combination thereof. It also involves administering a second fatty acid compound to said woman during a period which begins at least at about the tenth week of pregnancy. The second fatty acid is selected from the group consisting of docosahexaenoic acid compound, an omega-3 fatty acid, and omega-2 fatty acid, a derivative thereof and a combination thereof, and said second fatty acid compound being provided to the woman together with said first fatty acid compound. The weight range of said first fatty acid compound to said second fatty acid compound is about 1:0.1 to 10.

In another embodiment of the present invention subject matter, a method for enriching the breast milk of a woman wishing to optimize or who is concerned about the neurological development of the infant she breast-feeds comprises administering a first fatty acid compound in a range of about 10 mg to 100 mg to the woman during a period which begins at least at about the tenth week of pregnancy. This first fatty acid compound is selected from the group consisting of a linoleic acid compound, a linolenic acid compound, a derivative thereof and a combination thereof. It also involves administering a second fatty acid compound to said woman during a period which begins at least at about the tenth week of pregnancy in a range of 10 mg to 100 mg respectively for linoleic and linolenic acids. The second fatty acid is selected from the group consisting of docosahexaenoic acid compound, an omega-3 fatty acid, and omega-2 fatty acid, a derivative thereof and a combination thereof, and said second fatty acid compound being provided to the woman together with said first fatty acid compound. The weight range of said first fatty acid compound to said second fatty acid compound is about 1:0.1 to 10.

In a further embodiment of the inventive subject matter, a method for enriching the breast milk of a woman to optimize the neurological development of the infant she breast-feeds comprises administering a first fatty acid compound to the woman during a period which begins at least at about the tenth week of pregnancy and ends at the conclusion of breast-feeding or continues on as a nutritional supplement for the mother in a range of 10 mg to 100 mg. This first fatty acid compound is selected from the group consisting of a linoleic acid compound, a linolenic acid compound, a derivative thereof and a combination thereof. It also involves administering a second fatty acid compound to said woman during a period which begins at least at about the tenth week of pregnancy. The second fatty acid is selected from the group consisting of docosahexaenoic acid compound, an omega-3 fatty acid, and omega-2 fatty acid, a derivative thereof and a combination thereof, and said second fatty acid compound being provided to the woman together with said first fatty acid compound. It also involves administering a nutritional compound to said woman during a period which begins at least at about the tenth week of pregnancy. This compound is selected from a group consisting of a vitamin compound, a biologically-acceptable mineral compound, a derivative thereof and a combination thereof, and said nutritional compound being administered together with said first and said second fatty acid compounds. The weight range of said first fatty acid compound to said second fatty acid compound is about 1:0.1 to 10.

In a further embodiment of the inventive subject matter, a method for enriching the to a female mammal for enriching the milk of said female mammal to optimize neurological development of the neonate, which comprises: administering a first fatty acid compound to the woman during a period commencing at least at about the tenth week of pregnancy and terminating at the conclusion of breast-feeding, said first fatty acid compound being selected from the group consisting of a linoleic acid compound, a linolenic acid compound, a derivative thereof and a combination thereof; administering a second fatty acid compound to said woman during the period commencing at least at about the tenth week of pregnancy and terminating at the conclusion of breast-feeding, said second fatty acid compound being selected from the group consisting of a docosahexaenoic acid compound, an omega-3 fatty acid, and omega-2 fatty acid, a derivative thereof and a combination thereof, and said second fatty acid compound being provided to the woman together with said first fatty acid compound; and wherein the weight ratio of said first fatty acid compound to said second fatty acid compound is about 1:0.1 to 10.

In a further embodiment of the inventive subject matter, a method for enriching the milk of a female mammal to optimize neurological development of a neonate being nursed by the female mammal, which comprises administering a first fatty acid compound to the female mammal during a period commencing at least at about the tenth week of gestation, said first fatty acid compound being selected from the group consisting of a linoleic acid compound, a linolenic acid compound, a derivative thereof and a combination thereof; administering a second fatty acid compound to said female mammal during the period commencing at least at about the tenth week of gestation, said second fatty acid compound being selected from the group consisting of a docosahexaenoic acid compound, an omega-3 fatty acid, and omega-2 fatty acid, a derivative thereof and a combination thereof, and said second fatty acid compound being provided to the female mammal together with said first fatty acid compound; and wherein the weight ratio of said first fatty acid compound to said second fatty acid compound is about 1:0.1 to 10.

DETAILED DESCRIPTION OF THE INVENTION

As used herein, "nutritional stores" refers to the levels of vitamins, minerals and other nutrients which will be available for use by the mother, developing embryo, fetus and newborn infant.

"Nutritional status" refers to the presence or absence of any nutrient deficiency, or in other words, the extent to which physiological nutrient demands are being satisfied such that deficiency is avoided.

"Optimize neurological development" refers to attainment of the highest degree of neurological development possible through natural processes without the use of any unnatural substances or procedures, such as drugs, surgery and the like.

"Biologically active substance" refers to any substance or substances comprising a drug, active therapeutic substance, metabolite, medicament, vitamin, or mineral, any substance used for treatment, prevention, diagnosis, cure or mitigation of disease or illness, any substance which affects anatomical structure or physiological function, or any substance which alters the impact of external influences on an animal, or metabolite thereof, and as used herein, encompasses the terms "active substance", "therapeutic substance", "agent", "active agent", "active therapeutic agent", "drug", "medication", "medicine", "medicant", and other such similar terms.

"Specific physiological needs" refers to the unique requirements for certain levels of certain nutrients by one class of persons, such as lactating women, pregnant women, etc., as distinguished from other classes.

"Biologically-acceptable" refers to being safe for human consumption.

"Neonate" refers to the offspring of a female mammal that is nursed by said female mammal and has not yet been weaned.

The compositions of the present inventive subject matter provide several specific new and unexpected benefits. First, the formulations ensure that both the mother and her infant or infants are provided with adequate energy during the period of lactation. Secondly, the formulations allow the mother to maintain adequate fatty acid stores for both her own use and for incorporation into her breast milk as her supplies are depleted during lactation. Thirdly, the fatty acids optimize the neurological development of the infant consuming the breast milk. Fourthly, when administered prior to lactation, the present compositions prepare women for the increased physiological demands and stresses to be placed upon their bodies. Finally, the present compositions help women recover from pregnancy and lactation and prepare women for additional pregnancies and subsequent lactation.

Thus, the inventive subject matter provides a composition designed to be administered to a woman for the purpose of both enriching her breast milk for the benefit of her child and also to directly benefit the woman. In fact, in some cases, the formulations may allow a woman to breast-feed her infant where in the absence of taking the present composition breast-feeding would have been either unsafe or outright impossible. Infants consuming the enriched breast milk, as described herein, will experience optimal neurological development. Further, the present composition will help a post-partum woman to recover from her pregnancy and labor quickly and efficiently by providing her with the fatty acids lost in pregnancy and lactation. In addition, the present composition will place a woman in optimal condition for an additional pregnancy and the lactation that will follow by helping her increase her nutritional stores of critical nutritional compounds.

The present inventive subject matter is based, in part, on the discovery that when compositions having certain fatty acids, in certain amounts and proportions to one another, are administered to women prior to and during lactation, infants who consume the breast milk of said women will achieve optimized neurological development. In particular, supplementing the mother's diet with certain fatty acids for a period beginning at ten weeks after conception and either ending when lactation ceases or being continued as a supplement will not only optimize the neural development of the breast-feeding infant, but also ensure that the mother has adequate essential fatty acids for her own use. The fatty acid supplement may also further contain vitamins and minerals to confer added health benefits to the infant and mother. In addition to benefitting a breast-feeding human infant, the present invention can also benefit the offspring of non-human mammals that are nursed by their mothers. The composition of the present invention could be administered to a mammal in animal feed, pill form, or other appropriate dosage forms to such mammals.

Without being limited by theory, the present compositions stimulate the production of breast milk which is enriched with essential fatty acids in amounts which optimize infant neurological development. These compositions achieve such enrichment of the breast milk through one or more natural biological pathways. For example, the arachidonic acid cascade may play a significant role in the enrichment of the breast milk. Specifically, in the arachidonic acid cascade, linoleic acid is converted first to gamma-linolenic acid and then to further metabolites such as dihomo-gamma-linolenic acid and arachidonic acid which are precursors of 1 or 2 series prostaglandin respectively, as shown in the outline below:

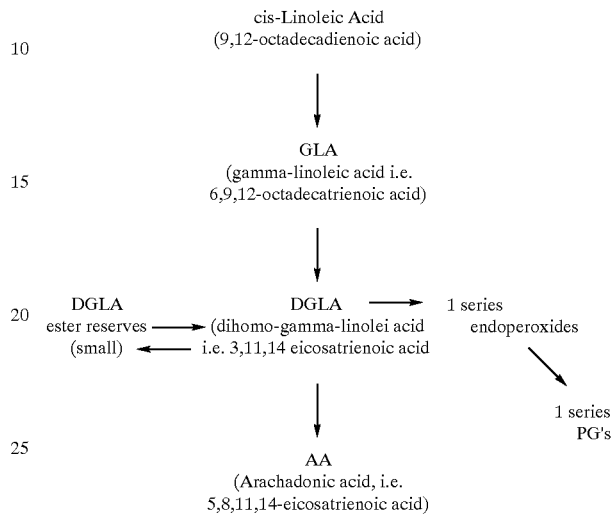

The present composition contains at least two fatty acid compounds. The first fatty acid compound is selected from the group consisting of a linoleic acid compound, a linolenic acid compound, derivatives thereof and combinations thereof. The second fatty acid compound is selected from the group consisting of a docosahexaenoic acid compound, an omega-3 fatty acid compound, an omega-2 fatty acid compound, derivatives thereof and combination thereof. Moreover, when the first fatty acid compound is linolenic acid or a derivative thereof and the second fatty acid compound is an omega-3 fatty acid, said omega-3 fatty acid is not linolenic acid or a derivative thereof. It is also preferred that when the first fatty acid compound is linoleic acid or a derivative thereof and the second fatty acid compound is an omega-2 fatty acid, said omega-2 fatty acid is not linoleic acid or a derivative thereof.

The two fatty acid compounds are present in the composition in critical proportions to one another. Preferably, the weight ratio of the first fatty acid to the second fatty acid is about 1:0.001 to 50. More preferably, the weight ratio of the first fatty acid compound to the second fatty acid compound is about 1:0.1 to 10. Even more preferably, the weight ratio of the first fatty acid compound to the second fatty acid compound is about 1:0.9 to 2.5. Most preferably, the weight ratio of the first fatty acid compound to the second fatty acid compound is about 1:1 to 2.

The fatty acids of the present inventive subject matter may be used as such or as biologically acceptable and physiologically equivalent derivatives as, for example, detailed later herein. Reference to any of the fatty acids including reference in the claims is to be taken as including reference to the acids when in the form of such derivatives. Equivalence is demonstrated by entry into the biosynthetic pathways of the body as evidenced by effects corresponding to those of the acids themselves or their natural glyceride esters. Thus, indirect identification of useful derivatives is by their having the valuable effect in the body of the fatty acid itself, but conversion, for example, of gamma-linolenic acid to dihomo-gamma-linolenic acid and on to arachidonic acid can be shown directly by gas chromatographic analysis of concentrations in blood, body fat, or other tissue by standard techniques, well known to persons of ordinary skill in the art to which the present inventive subject matter pertains.

Derivatives of linoleic acid, as used in the present inventive subject matter, include, without limitation, salts of linoleic acid, alkaline salts of linoleic acid, esters of linoleic acid, and combinations thereof. Derivatives of linolenic acid, as used in the present inventive subject matter, include, without limitation, salts of linolenic acid, alkaline salts of linoleic acid, esters of linoleic acid, and combinations thereof. The salts and alkaline salts herein refer to those regularly used organic or inorganic salts which are acceptable for pharmaceutical use. Non-limiting exemplary linolenic acids include gamma-linoleic acid and dihomo-gamma-linolenic acid.

The fatty acids of the present inventive subject matter may be from any source, including, without limitation, natural or synthetic oils, fats, waxes or combinations thereof. Moreover, the fatty acids herein may be derived, without limitation, from non-hydrogenated oils, partially hydrogenated oils, fully hydrogenated oils or combinations thereof. Non-limiting exemplary sources of fatty acids include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof. Specific non-limiting exemplary fish or marine oil sources include shellfish oil, tuna oil, mackerel oil, salmon oil, menhaden, anchovy, herring, trout, sardines or combinations thereof. Preferably, the source of the fatty acids is fish or marine oil, soybean oil or flaxseed oil.

The present composition may optionally contain additional vitamins and biologically-acceptable minerals. Non-limiting exemplary vitamins and biologically acceptable minerals and their derivatives thereof for inclusion in the present compositions include vitamin A, B vitamins, vitamin C, vitamin D, vitamin E, vitamin K, folic acid, iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

When vitamin C is present in the composition of the present inventive subject matter, it is preferably present in an amount ranging from about 10 mg to about 500 mg. More preferably, the vitamin C is present in an amount ranging from about 25 mg to about 400 mg. Even more preferably, the vitamin C is present an immediate release form in an amount ranging from about 25 mg to about 50 mg. Most preferably, the vitamin C is present in a controlled release form in an amount ranging from about 250 mg to about 500 mg.

When vitamin E is present in the composition of the present inventive subject matter, it is preferably present in an amount ranging from about 5 mg to about 500 mg. More preferably, the vitamin E is present in an amount ranging from about 10 mg to about 400 mg. Even more preferably, the vitamin E is present in a controlled release form in an amount ranging from about 250 mg to about 400 mg. Most preferably, the vitamin E is present in an immediate release form in an amount ranging from about 10 mg to about 50 mg.

Vitamin $B_6$ may also be present in the composition of the present inventive subject matter. Vitamin $B_6$ is preferably present in an amount ranging from about 10 mg to about 200 mg. More preferably, vitamin $B_6$ is present in an amount ranging from about 20 mg to about 125 mg. Even more preferably, vitamin B6 is present in an immediate release form in an amount ranging from 20 mg to about 50 mg. Most preferably, vitamin $B_6$ is present in a controlled release form in an amount ranging from 50 mg to about 125 mg.

Folic acid may also be incorporated into the composition of the present inventive subject matter. When folic acid is present in the composition, it is preferably present in an amount ranging from about 0.1 mg to about 3 mg. More preferably, folic acid is present in an immediate release form in an amount ranging from about 0.1 mg to about 2 mg. Even more preferably, folio acid is present in a controlled release form in an amount ranging from about 1.5 mg to about 3 mg.

Calcium is preferably present in the composition of the present inventive subject matter in an amount ranging from about 100 mg to about 2,500 mg. More preferably, calcium is present in an amount ranging from about 100 mg to about 1,000 mg. Even more preferably, calcium is present in an immediate release form in an amount ranging from about 100 mg to about 500 mg. Most preferably, calcium is present in a controlled release form in an amount ranging from about 500 mg to about 2,000 mg.

Magnesium is preferably present in the composition of the present inventive subject matter in an amount ranging from about 25 mg to about 400 mg. More preferably, magnesium is present in the composition of the present inventive subject matter in an immediate release form in an amount ranging from about 25 mg to about 100 mg. Even more preferably, magnesium is present in the composition of the present inventive subject matter in a controlled release form in an amount ranging from about 100 mg to about 400 mg.

The composition of the present inventive subject matter may also include one or more biologically active substance. The biologically active substances incorporated into the present inventive subject matter are nonteratogenic to protect the unborn fetus. For example, without limitation, the biologically active substance may be a lactogen compound, a derivative of a lactogen compound or combinations thereof. Derivatives of lactogen compounds include, without limitation, salts of lactogen compounds, alkaline salts of lactogen compounds, esters of lactogen compounds and combinations thereof.

Various additives may be incorporated into the present composition. Optional additives of the present composition include, without limitation, starches, sugars, fats, antioxidants, amino acids, proteins, derivatives thereof or combinations thereof.

It is also possible in the nutritional composition of the present inventive subject matter for the dosage form to combine various forms of release, which include, without limitation, immediate release, extended release, pulse release, variable release, controlled release, timed release; sustained release, delayed release, long acting, and combinations thereon. The ability to obtain immediate release, extended release, pulse release, variable release, controlled release, timed release, sustained release, delayed release, long acting characteristics and combinations thereof is performed using well known procedures and techniques available to the ordinary artisan. Each of these specific techniques or procedures for obtaining the release characteristics does not constitute an inventive aspect of this inventive subject matter all of which procedures are well known to those of ordinary skill in the art. As used herein, a "controlled release form" means any form having at least one component formulated for controlled release. As used herein, "immediate release form" means any form having all its components formulated for immediate release.

Any biologically-acceptable dosage form, and combinations thereof, are contemplated by the inventive subject matter. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, animal feeds, cereals, cereal coatings, foods, nutritive foods, functional foods and combinations thereof. The preparation of the above dosage forms are well known to persons of ordinary skill in the art.

The following procedures represent, without limitation, of acceptable methods of preparing formulations falling within the scope of the inventive subject matter. For example, animal feed may be by methods well known to persons of ordinary skill in the art. Animal feeds may be prepared by mixing the formulation with binding ingredients to form a plastic mass. The mass is then extruded under high pressure to form tubular (or "spaghetti-like") structures that are cut to pellet size and dried.

Quick dissolve tablets may be prepared, for example, without limitation, by mixing the formulation with agents such as sugars and cellulose derivatives, which promote dissolution or disintegration of the resultant tablet after oral administration, usually within 30 seconds.

Cereal coatings may be prepared, for example, without limitation, by passing the cereal formulation, after it has been formed into pellets, flakes, or other geometric shapes, under a precision spray coating device to deposit a film of active ingredients, plus excipients onto the surface of the formed elements. The units thus treated are then dried to form a cereal coating.

For example, health bars may be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example, without limitation, may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are well versed in the processes and the machinery used as the chewable dosage form is a very common dosage form in the pharmaceutical industry.

Film coated tablets, for example, without limitation, may be prepared by coating tablets using techniques such as rotating pan coating methods or air suspension methods to deposit a contiguous film layer on a tablet. This procedure is often done to improve the aesthetic appearance of tablets, but may also be done to improve the swallowing of tablets, or to mask an obnoxious odor or taste, or to improve to usual properties of an unsightly uncoated tablet.

Compressed tablets, for example, without limitation, may be prepared by mixing the formulation with excipients intended to add binding qualities to disintegration qualities. The mixture is either directly compressed or granulated then compressed using methods and machinery quite well known to those in the industry. The resultant compressed tablet dosage units are then packaged according to market need, i.e., unit dose, rolls, bulk bottles, blister packs, etc.

The present inventive subject matter contemplates nutritional compositions formulated for administration by any route, including without limitation, oral, buccal, sublingual, rectal, parenteral, topical, inhalational, injectable and transdermal. The physicochemical properties of nutritional compositions, their formulations, and the routes of administration are important in absorption. Absorption refers to the process of nutritional composition movement from the site of administration toward the systemic circulation. Most orally administered nutritional compositions are in the form of tablets or capsules primarily for convenience, economy, stability, and patient acceptance. They must disintegrate and dissolve before absorption can occur. Using the present inventive subject matter with any of the above routes of administration or dosage forms is performed using well known procedures and techniques available to the ordinary skilled artisan.

The present inventive subject matter contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

The plasticizers used in the dissolution modifying system are preferably previously dissolved in an organic solvent and added in solution form. Preferred plasticizers may be selected from the group consisting of diethyl phthalate, diethyl sebacate, triethyl citrate, cronotic acid, propylene glycol, butyl phthalate, dibutyl sebacate, caster oil and mixtures thereof, without limitation. As is evident, the plasticizers may be hydrophobic as well as hydrophilic in nature. Water-insoluble hydrophobic substances, such as diethyl phthalate, diethyl sebacate and caster oil are used to delay the release of water-soluble vitamins, such as vitamin $B_6$ and vitamin C. In contrast, hydrophilic plasticizers are used when water-insoluble vitamins are employed which aid in dissolving the encapsulated film, making channels in the surface, which aid in nutritional composition release.

The composition of the present inventive subject matter may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period.

The compositions of the present invention are intended for use by humans and other mammals. The dosages are adjusted according to body weight and thus may be set forth herein on a per body weight basis. For example, if the formula specifies a range of about 10–1000 mg for a 55 kg individual, that range would be adjusted for a 35 kg individual to about 6.3–63 mg (e.g., the lower range limit=(35 kg/55 kg) *10 mg=6.3 mg). Decimal amounts may be rounded to the nearest whole number. In the above manner the present compositions may thus be adapted to be suitable for any individual, including any mammal, regardless of its size.

The present composition is adapted to meet the specific physiological needs of a breast-feeding mother. For example, the formulations may focus on special nutritional needs of the mother that are not generally addressed in prenatal supplements, such as essential fatty acids, iron and calcium, without limitation. The iron and calcium, when present, are provided in amounts to optimize nutritional benefit to the mother, while minimizing unpleasant side effects which may accompany overly large doses. The formulation can be further tailored based upon the specific needs, genetic predispositions or identified deficiencies of women. Moreover, the present composition can be used as one component of a prescribed therapy.

Biologically-acceptable calcium compounds include, but are not limited to, any of the well known calcium supplements, such as calcium carbonate, calcium sulfate, calcium oxide, calcium hydroxide, calcium apatite, calcium citrate-malate, bone meal, oyster shell, calcium gluconate, calcium lactate, calcium phosphate, calcium levulinate, and the like.

Biologically-acceptable magnesium compounds which may be incorporated into the present inventive subject matter include, but are not limited to, magnesium stearate, magnesium carbonate, magnesium oxide, magnesium hydroxide and magnesium sulfate.

The compositions of the inventive subject matter may be provided in a blister pack or other such pharmaceutical package, without limitation. Further, the compositions of the present inventive subject matter may further include or be accompanied by indicia allowing women to identify the compositions as products for persons planning to or currently breast-feeding their infants. The indicia may further additionally include an indication of the above specified time periods for using said compositions.

The composition of the present inventive subject matter is preferably administered during a period commencing no later than at least the tenth week of pregnancy. More preferably, the composition is administered during a period of time commencing on about the tenth week of pregnancy and continuing through to completion of breast-feeding or continuing on as a nutritional supplement for the mother.

The present inventive subject matter includes a method for enriching the breast milk of women to optimize neurological development of infant's breast-fed by said women. The methods include administration of the present composition to women during a critical period. The critical period of administration is the period commencing at least at about the tenth week of pregnancy and terminating at the conclusion of breast-feeding or continuing on as a nutritional supplement for the mother.

The present composition and method may increase lactogenesis or the quantity of breast milk produced during lactation. Further, the compositions and methods may prevent or at least minimize fatty acid deficiency in lactating women. The quality of breast milk may also be improved by the compositions and methods. Moreover, the duration of the period of lactation may be extended by the present compositions and methods. Thus, women who would have difficulty breast-feeding for more than four weeks after pregnancy when not taking the present composition, could breast-feed for more than four weeks after pregnancy when taking the present composition.

The foregoing is considered as illustrative only of the principles of the inventive subject matter. Further, since numerous modifications and changes will readily occur to those skilled in the art, it is not desired to limit the inventive subject matter to the exact construction and operation shown and described, and accordingly all suitable modifications and equivalents may be resorted to, falling within the scope of the inventive subject matter.

The following examples are illustrative of preferred embodiments of the inventive subject matter and are not to be construed as limiting the inventive subject matter thereto. All percentages are based on the percent by weight of the final delivery system or formulation prepared unless otherwise indicated and all totals equal 100% by weight.

EXAMPLES

Example 1

The following formulations are used to prepare compositions for administration to women prior to and during lactation:

| Component (in mg unless otherwise indicated) | Formula I | Formula II | Formula III |
| --- | --- | --- | --- |
| Linoleic Acid | 10 | 100 | 20 |
| Linolenic Acid | 10 | 100 | 20 |
| Omega-3 Fatty Acid | 10 | 10 | 50 |
| Omega-2 Fatty Acid | — | — | 50 |
| Vitamin C | 25 | 400 | 700 |
| Vitamin E (I.U.) | 10 | 400 | 200 |
| Vitamin A (I.U.) | 2700 | 2700 | 2700 |
| Vitamin $D_3$ (I.U.) | 400 | 400 | 400 |
| Vitamin $B_6$ | 20 | 125 | 20 |
| Iron | 90 | 90 | 90 |
| Calcium | 2500 | 400 | 1000 |
| Microcrystalline Cellulose | 200 | 200 | 200 |
| Starch | 200 | 200 | 200 |
| Silicon Dioxide | 3 | 5 | 5 |
| Magnesium Stearate | 10 | 12 | 15 |

Example 2

The following compositions are used to prepare controlled release products for administration to women prior to and during lactation:

| Component (in mg unless otherwise indicated) | Controlled Release Formula A | Controlled Release Formula B |
|---|---|---|
| Linoleic Acid | 20 | 20 |
| Linolenic Acid | 20 | 20 |
| Omega-3 Fatty Acid | 50 | 50 |
| Omega-2 Fatty Acid | 50 | 50 |
| Vitamin C | 250 | 400 |
| Vitamin B (I.U.) | 200 | 400 |
| Vitamin A (I.U.) | 2700 | — |
| Vitamin $D_3$ (I.U.) | 400 | — |
| Vitamin $B_6$ | 125* | 125* |
| Iron | 90* | — |
| Calcium | 500 | 100 |
| Microcrystalline Cellulose | 200 | 200 |
| Starch | 200 | 200 |
| Silicon Dioxide | 5 | 1 |
| Magnesium Stearate | 15 | 15 |
| Ethylcellulose | 60 | 60 |
| Folic Acid | — | 1 |
| Magnesium | — | 25 |

*formulated for controlled release

Example 3

The following compositions are used to prepare products for administration to women prior to and during lactation:

| Component | IV | V | VI | VII | VIII | IX |
|---|---|---|---|---|---|---|
| Linoleic Acid | 10 | 100 | 20 | 10 | 100 | 20 |
| Linolenic Acid | 10 | 100 | 20 | 10 | 100 | 20 |
| Omega-3 Fatty Acid | 10 | 10 | 50 | 10 | 10 | 50 |
| Omega-2 Fatty Acid | — | — | 50 | — | — | 50 |
| Vitamin B6 | 20 | 125 | 20 | 20 | 125 | 20 |
| Folic Acid | 0.1 | 3 | 1 | 0.1 | 3 | 1 |
| Calcium | 100 | 400 | 1000 | 100 | 1000 | 1000 |
| Magnesium | — | — | — | 25 | 400 | 25 |
| Vitamin C | — | — | — | 25 | 400 | 400 |
| Vitamin E (I.U.) | — | — | — | 10 | 400 | 400 |
| Microcrystalline Cellulose | 100 | 100 | 200 | 100 | 100 | 100 |
| Starch | 100 | 100 | 200 | 100 | 100 | 100 |
| Silicon Dioxide | 0.3 | 0.7 | 1 | 0.3 | 1 | 1 |
| Magnesium Stearate | 3 | 7 | 15 | 3 | 15 | 15 |
| Lactose | 100 | — | — | 100 | — | — |
| Ethylcellulose | — | — | — | — | — | — |

The above components are in mg unless otherwise indicated. Tablets incorporating the above formulations are prepared using conventional methods and materials known in the pharmaceutical art. The resulting nutritional compositions were recovered and stored for future use.

Example 4

A soft gelatin supplement may be prepared, by first combining mineral oil and soybean oil in a first vessel and blending it to form a uniform oil mixture, heating the oil mixture to 45 degrees Celsius, and then adding propylene glycol. In a second vessel preheated to 70 degrees Celsius, yellow beeswax and soybean oil are added and blended until a uniform wax mixture is formed. The wax mixture is cooled to 35 degrees Celsius and then added to the oil mixture. To this combined oil and wax mixture, folic acid, vitamin $B_6$, iron, magnesium, and calcium are then added and blended together to form a uniform biologically active mixture. The mixture is then cooled to 30 degrees Celsius to form a viscous biologically active core composition, after which time the composition is ready for encapsulation in a soft gelatin shell.

A soft gelatin shell is prepared by heating purified water in a suitable vessel and then adding gelatin. This water gelatin mixture is mixed until the gelatin is fully dissolved, and then glycerin, preservative, one or more flavors, and one or more colorants are added. This gelatin mixture is blended well and cooled. The shells are then filled with the core composition and formed in accordance with soft gelatin techniques commonly used and well known to persons of skill in the art.

The inventive subject matter being thus described, it will be apparent that the same may be varied in many ways. Such variations are not to be regarded as a departure from the spirit and scope of the inventive subject matter, and all such modifications are intended to be within the scope of the appended claims.

We claim:

1. A composition for administration to a woman for enriching the breast milk of said woman to optimize neurological development of an infant breast-fed by the woman, which comprises:
   a) about 10 mg to 100 mg of a first fatty acid compound for each compound selected from the group consisting of a linoleic acid compound, a linolenic acid compound, a derivative thereof and a combination thereof;
   b) about 10 mg to 1000 mg of a second fatty acid compound selected from the group consisting of a docosahexaenoic acid compound, an omega-3 fatty acid, an omega-2 fatty acid, a derivative thereof and a combination thereof;
   c) about 10 mg to 125 mg of a vitamin $B_6$ compound or derivative thereof;
   d) about 0.1 mg to 3 mg of a folic acid compound or derivative thereof;
   e) about 100 mg to 2,000 mg of a calcium compound or derivative thereof;
   f) about 25 mg to 500 mg of a vitamin C compound or derivative thereof;
   g) about 10 mg to 400 mg of a vitamin E compound or derivative thereof; and
   wherein the weight ratio of said first fatty acid compound to said second fatty acid compound is about 1:0.1 to 10, said weight ratio specifically formulated to enrich the breast milk of the woman to optimize neurological development of an infant breast-fed by the woman.

2. The composition of claim 1, wherein said composition additionally contains a biologically active substance.

3. The composition of claim 2, wherein the biologically active substance is a lactogen compound or derivative thereof.

4. The composition of claim 1, wherein said composition is administered during a period commencing no later than the tenth week of pregnancy.

5. The composition of claim 1, wherein said composition is administered during a period of time commencing at least at about the tenth week of pregnancy.

6. The composition of claim 1, wherein said composition is adapted to meet specific physiological needs of a breast-feeding mother.

7. The composition of claim 1, wherein said composition is in an oral dosage form.

8. The composition of claim 7, wherein said oral dosage form is selected from the group consisting of immediate release, extended release, pulsed release, delayed release, controlled release and combinations thereof.

9. The composition of claim 7, wherein said oral dosage form is selected from the group consisting of a chewable tablet, quick dissolve tablet, an effervescent tablet, a hard gelatin capsule, a soft gelatin capsule, reconstitutable particles, microparticles, a suspension, an elixir, a caplet, a fortified food, pudding, yogurts, gelatin, cereal and combinations thereof.

10. The composition of claim 1, wherein said composition is administered once during a twenty four hour period of time.

11. The composition of claim 1, wherein said composition is administered at least twice during a twenty four hour period of time.

12. The composition of claim 1, wherein said composition increases lactogenesis.

13. The composition of claim 1, wherein said composition increases the quantity of breast milk produced during lactation.

14. The composition of claim 1, wherein said composition prevents deficiency of essential fatty acids in the woman.

15. The composition of claim 1, wherein said composition is provided with indicia indicating a time period of use.

16. The composition of claim 15, wherein said time period of use is prior to, during and after lactation.

17. The composition of claim 15, wherein said time period commences at about the tenth week of pregnancy.

18. The composition of claim 1, wherein said composition extends the duration of the period of lactation.

19. The composition of claim 1, wherein said composition improves quality of said breast milk.

20. The composition of claim 1, wherein said composition achieves enrichment of said breast milk through a natural biological pathway.

21. The composition of claim 1, additionally comprising a vitamin compound selected from the group consisting of a vitamin A compound, a B complex vitamin compound, a vitamin D compound, and combinations thereof.

22. The composition of claim 1, further comprising a biologically-acceptable mineral compound which is iron.

23. A composition for administration to a woman for enriching the breast milk of said woman to optimize neurological development of an infant breast-fed by the woman, which comprises:
   a) about 10 mg to about 100 mg of a first fatty acid compound for each compound selected from the group consisting of a linoleic acid compound, a linolenic acid compound, a derivative thereof and a combination thereof;
   b) about 10 mg to about 1000 mg of a second fatty acid compound for each compound selected from the group consisting of a docosahexaenoic acid compound, an omega-3 fatty acid compound, an omega-2 fatty acid compound, a derivative thereof and a combination thereof;
   c) a vitamin compound selected from the group consisting of about 10 mg to about 200 mg of a vitamin $B_6$ compound or derivative thereof, about 0.1 mg to about 3 mg of a folic acid compound or derivative thereof, about 25 mg to about 500 mg of a vitamin C compound or derivative thereof, about 10 mg to about 400 mg of a vitamin E compound or derivative thereof, and combinations thereof; and
   d) a biologically acceptable mineral compound which is selected from the group consisting of about 100 mg to about 2000 mg of a calcium compound or derivative thereof, about 25 mg to about 400 mg of a magnesium compound or derivative thereof, and combinations thereof;
   wherein the weight ratio of said first fatty acid compound to said second fatty acid compound is about 1:0.1 to 10, said weight ratio specifically formulated to enrich the breast milk of the woman to optimize neurological development of an infant breast-fed by the woman.

* * * * *